(12) United States Patent
Lu et al.

(10) Patent No.: US 10,806,810 B2
(45) Date of Patent: Oct. 20, 2020

(54) SELF-SHIELDING ACCELERATOR AND PET PLASTIC BOTTLE PRODUCTION LINE UTILIZING SAME

(71) Applicant: CGN DASHENG ELECTRON ACCELERATOR TECHNOLOGY CO., LTD., Suzhou (CN)

(72) Inventors: Jieping Lu, Suzhou (CN); Huanzheng Zhu, Suzhou (CN); Zhanghua Yu, Suzhou (CN)

(73) Assignee: CGN DASHENG ELECTRON ACCELERATOR TECHNOLOGY CO., LTD., Suzhou (CN)

( * ) Notice: Subject to any disclaimer, the term of this patent is extended or adjusted under 35 U.S.C. 154(b) by 281 days.

(21) Appl. No.: 15/758,411

(22) PCT Filed: Dec. 24, 2015

(86) PCT No.: PCT/CN2015/098700
§ 371 (c)(1),
(2) Date: Mar. 8, 2018

(87) PCT Pub. No.: WO2017/041388
PCT Pub. Date: Mar. 16, 2017

(65) Prior Publication Data
US 2018/0256763 A1    Sep. 13, 2018

(30) Foreign Application Priority Data
Sep. 11, 2015    (CN) .......................... 2015 1 0576112

(51) Int. Cl.
*A61L 2/08*    (2006.01)
*H05H 7/00*    (2006.01)
(Continued)

(52) U.S. Cl.
CPC .................. *A61L 2/087* (2013.01); *A61L 2/08* (2013.01); *B67C 3/02* (2013.01); *B67C 7/00* (2013.01);
(Continued)

(58) Field of Classification Search
CPC ..... A61L 2/087; A61L 2202/23; B65B 55/08; B67C 3/02; B67C 7/002; B67C 7/0073
(Continued)

(56) References Cited

U.S. PATENT DOCUMENTS 3,358,239 A * 12/1967 Siegfried ............... G21K 1/093
   315/500
5,483,122 A    1/1996 Derbenev et al.
(Continued)

FOREIGN PATENT DOCUMENTS

CN    2810601 Y       8/2006
CN    101160015 A  *  4/2008
(Continued)

OTHER PUBLICATIONS

Masayuki Kashiwagi and Yasuhisa Hoshi. "Electron beam Processing System and Its Application", Oct. 2012 [retrieved on Feb. 7, 2020], 8 pgs, Retrieved from the Internet: <URL: https://global-sei.com/technology/tr/bn75/pdf/75-09.pdf>. (Year: 2012).*

*Primary Examiner* — Stephen F. Gerrity
*Assistant Examiner* — Joshua G Kotis
(74) *Attorney, Agent, or Firm* — Boyle Fredrickson S.C.

(57) ABSTRACT

A self-shielding accelerator is provided, which includes an accelerator assembly, a high-frequency electrode plate, a rectification and voltage multiplication assembly, a solenoid-type transformer assembly, a cooling system assembly and a shielding steel cylinder. The self-shielding accelerator further includes a steel cylinder base connected to the shielding steel cylinder. The accelerator assembly is hori-
(Continued)

zontally fixed to the steel cylinder base. The rectification and voltage multiplication assembly is fixed to the steel cylinder base by a support plate. The high-frequency electrode plate and the solenoid-type transformer assembly are connected to the steel cylinder base through multiple horizontally arranged support columns. The cooling system assembly is fixed to the shielding steel cylinder. The self-shielding accelerator adopts a fully horizontal self-shielding structure, and can be seamlessly joined to the filling production line, which makes online radiation processing possible. A PET plastic bottle production line utilizing the accelerator is also provided.

6 Claims, 4 Drawing Sheets

(51) Int. Cl.
  *H05H 5/04* (2006.01)
  *B67C 3/02* (2006.01)
  *B67C 7/00* (2006.01)

(52) U.S. Cl.
  CPC .............. *H05H 5/045* (2013.01); *H05H 7/00* (2013.01); *A61L 2202/11* (2013.01); *A61L 2202/23* (2013.01); *H05H 2245/1225* (2013.01)

(58) Field of Classification Search
  USPC .............. 422/22; 250/453.11–455.11, 492.3; 53/425, 426, 167
  See application file for complete search history.

(56) References Cited

U.S. PATENT DOCUMENTS

| | | | | |
|---|---|---|---|---|
| 5,604,352 | A | * | 2/1997 | Schuetz ................... G21K 5/04 250/492.3 |
| 2002/0134946 | A1 | * | 9/2002 | Kiga ....................... H01J 33/00 250/396 R |
| 2005/0225224 | A1 | * | 10/2005 | Dally ....................... H01J 33/00 313/361.1 |
| 2007/0253861 | A1 | * | 11/2007 | Naka ....................... A61L 2/087 422/22 |
| 2009/0110613 | A1 | * | 4/2009 | Naka ....................... A61L 2/087 422/186 |
| 2010/0202918 | A1 | * | 8/2010 | Kobayashi .............. A61L 2/087 422/22 |
| 2011/0017920 | A1 | * | 1/2011 | Goer ........................ G21K 1/10 250/396 R |
| 2012/0145929 | A1 | * | 6/2012 | Nishino .................. A61L 2/087 250/492.3 |
| 2014/0027651 | A1 | * | 1/2014 | Kawasaki ................. A61L 2/08 250/453.11 |
| 2015/0108366 | A1 | * | 4/2015 | Kawasaki ................ G21K 5/04 250/453.11 |
| 2016/0229572 | A1 | * | 8/2016 | Yokobayashi .......... B65B 55/08 |

FOREIGN PATENT DOCUMENTS

| | | | |
|---|---|---|---|
| CN | 101160015 | A | 4/2008 |
| CN | 103536947 | A | 1/2014 |
| CN | 104302089 | A * | 1/2015 |
| CN | 104302089 | A | 1/2015 |
| CN | 104891409 | A | 9/2015 |
| CN | 105101605 | A | 11/2015 |
| JP | H10172796 | A | 6/1998 |

* cited by examiner

SELF-SHIELDING ACCELERATOR AND PET PLASTIC BOTTLE PRODUCTION LINE UTILIZING SAME

CROSS-REFERENCE TO RELATED APPLICATIONS

The present application is the national phase of International Application No. PCT/CN2015/098700, titled "SELF-SHIELDING ACCELERATOR AND PET PLASTIC BOTTLE PRODUCTION LINE UTILIZING SAME", filed on Dec. 24, 2015 which claims the benefit of priority to Chinese patent application No. 201510576112.6 titled "SELF-SHIELDING ACCELERATOR AND PET PLASTIC BOTTLE PRODUCTION LINE UTILIZING SAME", filed with the Chinese State Intellectual Property Office on Sep. 11, 2015, the entire disclosure of which applications are incorporated herein by reference.

TECHNICAL FIELD

This application relates to a self-shielding accelerator and a polyethylene terephthalate (PET) plastic bottle production line utilizing the accelerator, and belongs to the technical field of accelerator irradiation self-shielding accelerators.

BACKGROUND OF THE INVENTION

One of the critical technologies for aseptic filling of PET bottles is sterilization treatment, which is critical to the success of the aseptic filling. The sterilization scope covers packaging materials (PET bottles and caps). The conventional method for the sterilization treatment is generally a chemical method in which metabolism of bacterial enzyme system is interfered using the oxidizability of a strong oxidizing agent and the molecular structure of the protein of the bacterial enzyme so as to inactivate the bacterial enzyme. The agents commonly used at present include hydrogen peroxide, peracetic acid, chlorine dioxide solution, disinfecting solution and the like. The use of the chemical sterilization method has the following disadvantages.

1. The packaging materials, containers and the self-shielding accelerators may be contaminated by a certain amount of residue of the chemical agents, thus strict measures must be taken to control the residue, so as to ensure the safety of a final product.

2. The use of the chemical agent is accompanied by consumption of a large amount of water, influence on the environment as well as a requirement for supporting of a chemical agent station.

The radiation sterilization method is an effective method in which microorganisms in most substances are killed using electromagnetic waves generated by electromagnetic radiation. During irradiation, electron beams, X-rays or y-rays act on the microorganisms, and directly or indirectly destroy ribonucleic acids, proteins and enzymes of the microorganisms, thereby killing microorganisms, thus disinfection and sterilization are achieved. The radiation sterilization method is a pollution-free, residue-free sterilization method and is a green and environment-friendly technique. Especially for an electron beam sterilization method, electron beams are generated by an electron accelerator, and do not have a radiation source, thus is safer than cobalt 60. From the perspective of the sterilization dose, the dose provided by the electron accelerator is more accurate, thus the electron beam sterilization method is the tendency of development of the radiation sterilization method in future.

In view of the advantages of the radiation sterilization method, many issues caused by the use of the chemical sterilization method may be well addressed. Therefore, the idea of replacing the chemical sterilization method with the radiation sterilization method is valued by many companies having the PET bottle filling production line, and the feasibility of this alternative method is continuously explored by these companies. Limited by the prior manufacturing technology of electron accelerators, the accelerator body is fairly large and requires a building for shielding, thus it is impossible to apply the electron accelerators to the production line. With the rapid development of the manufacturing technology of the electron accelerators in recent years, a low-energy electron accelerator gradually tends to self-shielding and a miniaturized design, which makes online radiation processing (the online radiation processing means that the electron accelerator may be mounted to the production line) possible.

At present, relevant products are not yet available in the market. In order to further promote energy conservation and environmental protection, filling production line manufacturers urgently wish to develop a production line which sterilizes PET bottles utilizing the electron beams.

SUMMARY OF THE INVENTION

A technical issue to be addressed by the present application is to provide a self-shielding accelerator and a PET plastic bottle production line utilizing the accelerator. The self-shielding accelerator adopts a fully horizontal self-shielding structure and may be seamlessly joined to a filling production line, which makes online radiation processing possible.

In order to address the above technical issue, the following technical solutions are provided according to the present application.

A self-shielding accelerator is provided, which includes an accelerator assembly, a high-frequency electrode plate, a rectification and voltage multiplication assembly, a solenoid-type transformer assembly, a cooling system assembly and a shielding steel cylinder. The self-shielding accelerator further includes a steel cylinder base connected to the shielding steel cylinder. The accelerator assembly is horizontally fixed to the steel cylinder base. The rectification and voltage multiplication assembly is fixed to the steel cylinder base by a support plate. The high-frequency electrode plate and the solenoid-type transformer assembly are connected to the steel cylinder base through multiple horizontally arranged support columns. The cooling system assembly is fixed to the shielding steel cylinder.

Preferably, the support plate is further provided with an accelerator support block and an adjusting bolt, and the accelerator support block and the adjusting bolt are connected to the accelerator assembly.

Preferably, the shielding steel cylinder and the steel cylinder base are provided with multiple footings, and each of the footings is provided with a guide wheel cooperating with a track.

Preferably, one of the footings of the shielding steel cylinder is further provided with an electrical opening and closing assembly.

Preferably, the number of the support columns is four, and the four support columns are respectively provided at an upper end and a lower end of the steel cylinder base.

A polyethylene terephthalate plastic bottle production line utilizing the self-shielding accelerator described above is provided, and the PET plastic bottle production line includes a filling production line. A scanning box is provided between the filling production line and the self-shielding accelerator. The scanning box is seamlessly connected to an irradiation cavity of the filling production line via a step surface.

The present application has the following beneficial effects.

1. A concept of an embedded self-shielding structure is proposed in the present application. The self-shielding accelerator is seamlessly joined to the entire filling production line. The scanning box for the self-shielding accelerator according to the present application is joined to an opening surface of the production line directly, which may avoid leakage of radiation, thus the safety of the product is ensured.

2. In the present application, a fully horizontal structure is proposed in which an acceleration tube and a beam lead-out portion are integrated into the rectification and voltage multiplication assembly. Moreover, a steel cylinder for the acceleration tube and a steel cylinder for a high-voltage power supply, which are originally separated from each other, are integrated into one accelerator steel cylinder, and the shielding of the accelerator steel cylinder is also enhanced. Thus the space is greatly saved and the radiation protection requirements are taken into account.

3. In the present application, a new horizontal installation structure is provided and is provided four support columns. The four support columns are fixed to the steel cylinder base. The components, such as the high-frequency electrode plate and the solenoid-type transformer assembly, previously fixed to the main steel cylinder of the accelerator, are now fixed by means of the four support columns respectively. Thus the accelerator has advantages of a simpler structure and convenient maintenance. In this way, all critical components are fixed to the steel cylinder base together. In maintenance, as long as the main steel cylinder is opened, these critical components may be inspected and maintained.

4. The shielding structure according to the present application is divided into two portions, with one portion being a beam scanning system portion and another portion being an accelerator main body shielding portion. The beam scanning system portion is connected to a filling production line, to ensure the self-shielding accelerator to be seamlessly joined to the production line. The shielding body is an all-steel structure. The shielding steel cylinder may be electrically opened and closed through the beam scanning system portion and the accelerator main body shielding portion by means of the electrical opening and closing assembly Thus the self-shielding accelerator has advantages of a small volume, a good shielding effect, simple operation and so on, and the convenience of installation and maintenance is also greatly increased.

In the present application, the automatic control system is optimized, a one-touch operation mode is adopted, and the overall operability of the self-shielding accelerator is optimized. The operation is simple, safe and reliable, and the level of automation is high, which greatly reduces the requirements for the operators.

DETAILED DESCRIPTION OF EMBODIMENTS

The present application is further described in conjunction with the drawings of the specification.

Figure 1:
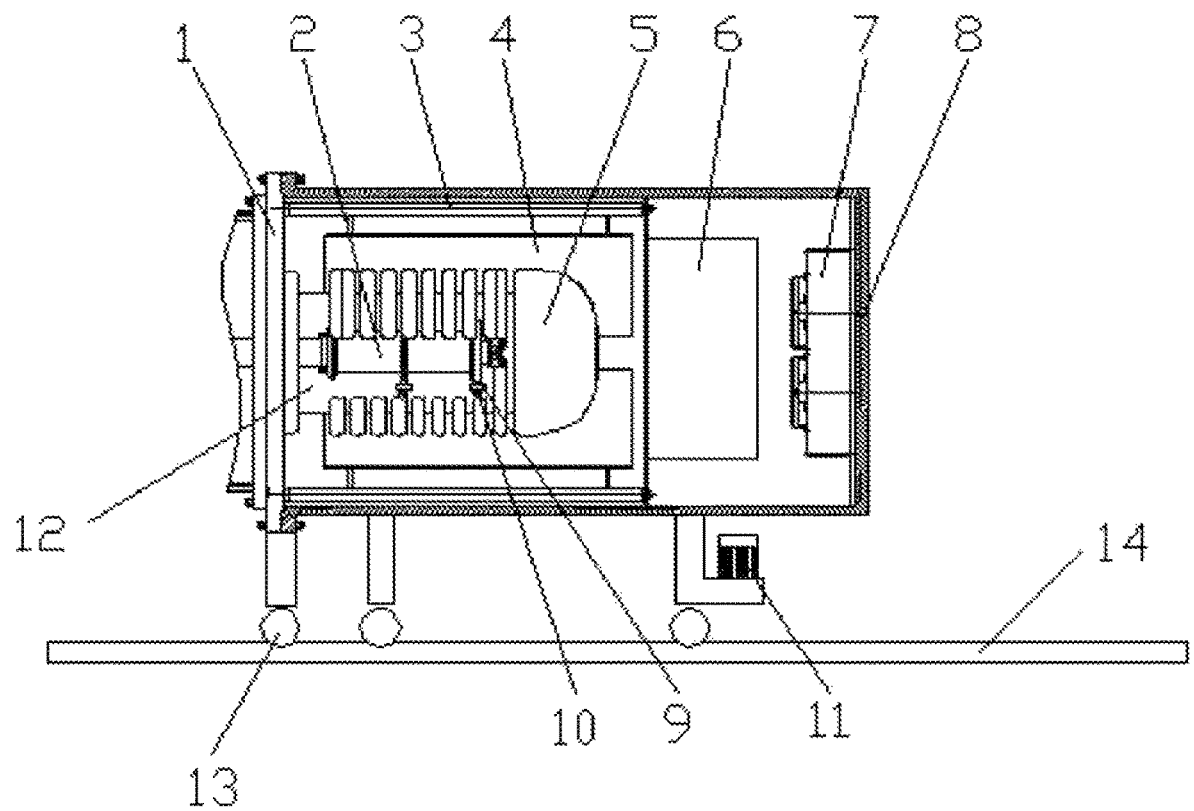
FIG. 1 is a side view of a self-shielding accelerator according to the present application.
Figure 2:
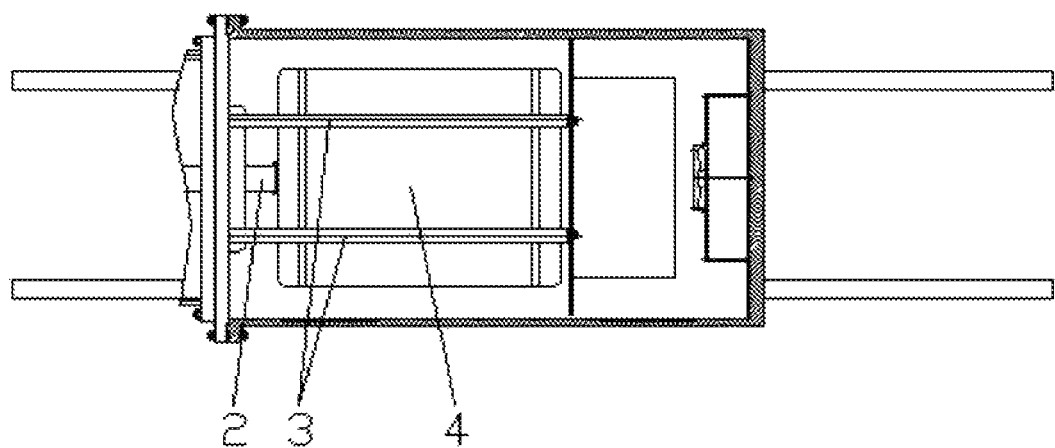
FIG. 2 is a top view of the self-shielding accelerator according to the present application.
Figure 3:
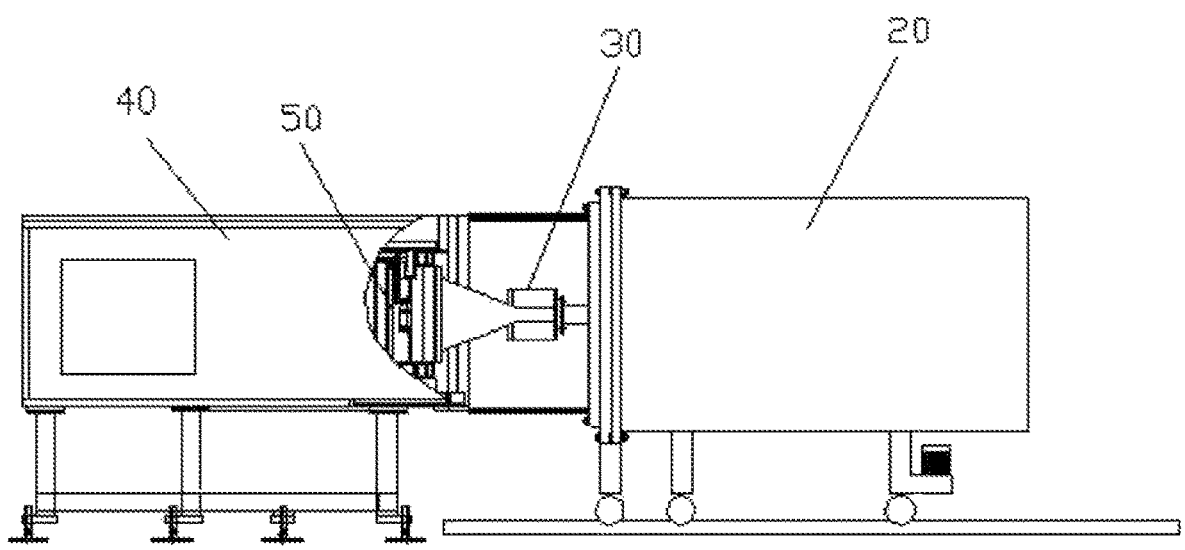
FIG. 3 is a side view of a PET plastic bottle production line according to the present application.
Figure 4:
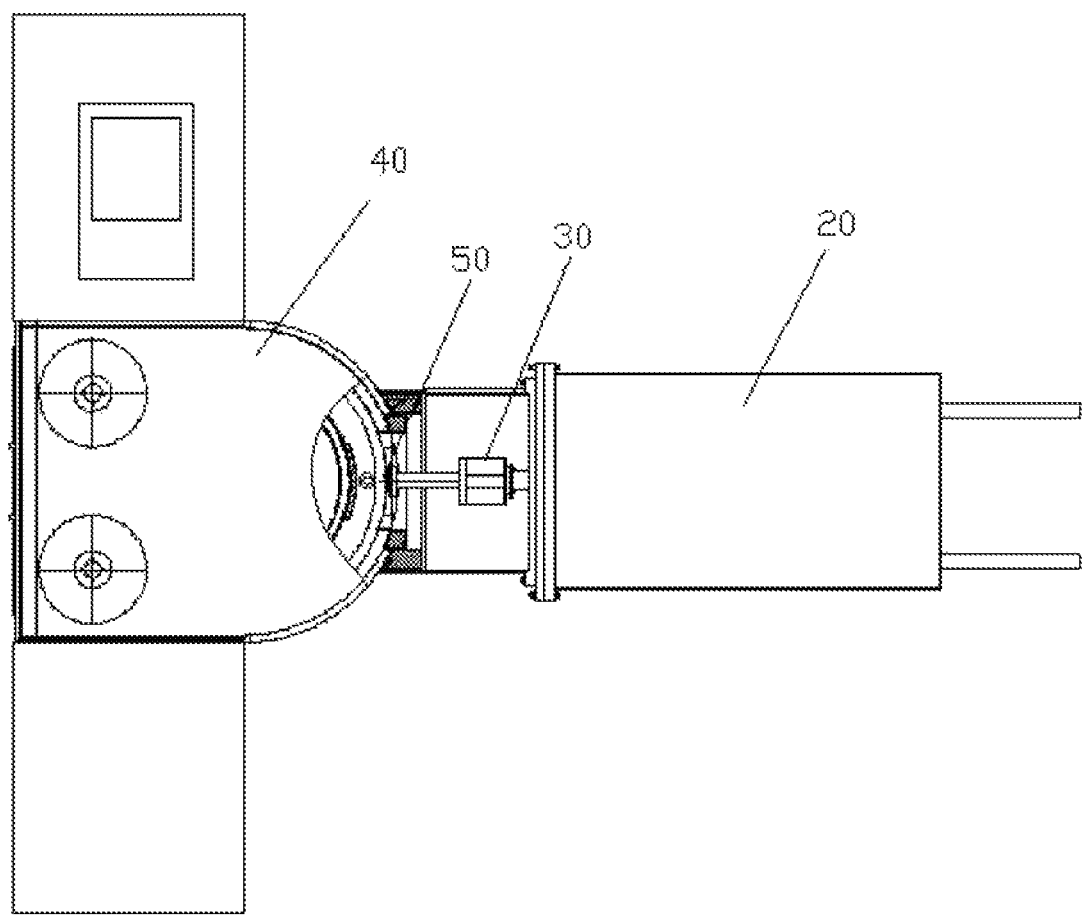
FIG. 4 is a top view of the PET plastic bottle production line according to the present application.

As shown in FIG. 1 and FIG. 2, a self-shielding accelerator includes an accelerator assembly 2, a high-frequency electrode plate 4, a rectification and voltage multiplication assembly 5, a solenoid-type transformer assembly 6, a cooling system assembly 7 and a shielding steel cylinder 8. The self-shielding accelerator further includes a steel cylinder base 1 connected to the shielding steel cylinder 8. The accelerator assembly 2 is horizontally fixed to the steel cylinder base 1. The rectification and voltage multiplication assembly 5 is fixed to the steel cylinder base 1 via a support plate 12. The high-frequency electrode plate 4 and the solenoid-type transformer assembly 6 are connected to the steel cylinder base 1 by multiple horizontally arranged support columns 3. The cooling system assembly 7 is fixed to the shielding steel cylinder 8.

In this embodiment, the steel cylinder base 1 is provided with four support columns 3, which are respectively provided at an upper end and a lower end of the steel cylinder base 1. The four support columns 3 are fixed to the steel cylinder base. The high-frequency electrode plate 4 and the solenoid-type transformer assembly 6, etc., which are previously fixed to the main steel cylinder of the accelerator, are now respectively fixed by means of the four support columns 3, thus having the advantages of a simple structure and convenient maintenance. In this way, all critical components are fixed to the steel cylinder base 1. In maintenance, as long as the main steel cylinder is opened, these critical components can be inspected and maintained. Thus, a new horizontal installation structure is provided.

The support plate 12 is further provided with an accelerator support block 9 and an adjusting bolt 10 which are connected to the accelerator assembly 2, which avoids the influence of deflection of an acceleration tube and ensures a horizontal position of the acceleration tube.

The shielding steel cylinder 8 and the steel cylinder base 1 are provided with multiple footings. Each of the footings is provided with a guide wheel 13 cooperating with a track 14. One of the footings of the shielding steel cylinder 8 is further provided with an electrical opening and closing assembly 11. The shielding structure is divided into two portions, with one portion being a beam scanning system portion and another portion being an accelerator main body shielding portion. The beam scanning system portion is connected to a filling production line, to ensure the self-shielding accelerator to be seamlessly joined to the production line. The shielding body is an all-steel structure. The shielding steel cylinder 8 may be electrically opened and closed through the beam scanning system portion and the accelerator main body shielding portion by means of the electrical opening and closing assembly 11. Thus, the self-shielding accelerator has advantages of a small volume, a good shielding effect, simple operation and so on, and the convenience of installation and maintenance is also greatly increased.

A PET plastic bottle production line using the self-shielding accelerator is further provided according to the present application, which includes a filling production line 40. A scanning box 30 is provided between the filling production line 40 and the self-shielding accelerator 20. The scanning box 30 is seamlessly connected to an irradiation cavity 50 of the filling production line 40 by a step surface. Thus the self-shielding accelerator is seamlessly joined to the entire filling production line. The scanning box for the self-shielding accelerator according to the present application is joined to an opening surface of the production line directly, which may avoid leakage of radiation, thus the safety of the product is ensured.

In conclusion, the self-shielding accelerator and the PET plastic bottle production line utilizing the accelerator are provided according to the present application. The self-shielding accelerator adopts a fully horizontal self-shielding structure, and can be seamlessly joined to the filling production line, which makes online radiation processing possible.

The basic principle, main features and advantages of the present application are shown and described hereinabove. It should be understood by the person skilled in the art that, the present application is not limited to the above embodiment. The above embodiment and the description in the specification are only intended to illustrate the principle of the present application. Various variations and improvements may be made to the present application without departing from the spirit and scope of the present application, and these variations and improvements are all deemed to fall into the scope of the present application as claimed. The scope of the present application as claimed is defined by the claims and equivalents thereof.

We claim:

1. A self-shielding accelerator, comprising:
an accelerator assembly,
a high-frequency electrode plate,
a rectification and voltage multiplication assembly,
a solenoid transformer assembly,
a cooling system assembly, and
a shielding steel cylinder,
wherein the self-shielding accelerator further comprises a steel cylinder base connected to the shielding steel cylinder, the accelerator assembly is horizontally fixed to the steel cylinder base, the rectification and voltage multiplication assembly is fixed to the steel cylinder base by a support plate, the high-frequency electrode plate and the solenoid transformer assembly are connected to the steel cylinder base through a plurality of horizontally arranged support columns, and the cooling system assembly is fixed to the shielding steel cylinder,
wherein the shielding steel cylinder and the steel cylinder base are provided with a plurality of footings, and each of the footings is provided with a guide wheel cooperating with a track,
wherein one of the footings of the shielding steel cylinder is further provided with an electrical opening and closing assembly.

2. The self-shielding accelerator according to claim 1, wherein the support plate is further provided with an accelerator support block and an adjusting bolt which are connected to the accelerator assembly.

3. The self-shielding accelerator according to claim 1, wherein the number of the support columns is four, and two of the four support columns are provided at an upper end of the steel cylinder base and the other two of the four support columns are provided at a lower end of the steel cylinder base.

4. A polyethylene terephthalate plastic bottle production line comprising the self-shielding accelerator according to claim 1, a filling production line, wherein a scanning box is provided between the filling production line and the self-shielding accelerator, and the scanning box is connected at a seamless connection to an irradiation cavity of the filling production line via a step surface.

5. A polyethylene terephthalate plastic bottle production line comprising the self-shielding accelerator according to claim 2, a filling production line, wherein a scanning box is provided between the filling production line and the self-shielding accelerator, and the scanning box is seamlessly connected to an irradiation cavity of the filling production line via a step surface.

6. A polyethylene terephthalate plastic bottle production line comprising the self-shielding accelerator according to claim 5, a filling production line, wherein a scanning box is provided between the filling production line and the self-shielding accelerator, and the scanning box is seamlessly connected to an irradiation cavity of the filling production line via a step surface.

* * * * *